(12) United States Patent  
Henry et al.

(10) Patent No.: US 11,446,426 B2  
(45) Date of Patent: Sep. 20, 2022

(54) COLLAPSIBLE LIQUID RESERVOIR

(71) Applicant: Hollister Incorporated, Libertyville, IL (US)

(72) Inventors: Jerome Anthony Henry, Castlebar (IE); William Kirwan Arnold, Gurnee, IL (US); Denise Gamblin, Leeds (GB); Keith Hobert Gausmann, Cary, NC (US); Maitreyee Mittal, Cary, NC (US); Scott Eric Liddle, Raleigh, NC (US); Anthony Scott Culbreth, Youngsville, NC (US)

(73) Assignee: Hollister Incorporated, Libertyville, IL (US)

( * ) Notice: Subject to any disclaimer, the term of this patent is extended or adjusted under 35 U.S.C. 154(b) by 69 days.

(21) Appl. No.: 16/626,972

(22) PCT Filed: Jun. 26, 2018

(86) PCT No.: PCT/US2018/039561  
§ 371 (c)(1),  
(2) Date: Dec. 27, 2019

(87) PCT Pub. No.: WO2019/005836  
PCT Pub. Date: Jan. 3, 2019

(65) Prior Publication Data  
US 2020/0215256 A1  Jul. 9, 2020

Related U.S. Application Data

(60) Provisional application No. 62/526,837, filed on Jun. 29, 2017.

(51) Int. Cl.  
*A61M 3/02* (2006.01)  
*B65D 21/08* (2006.01)

(52) U.S. Cl.  
CPC ........ *A61M 3/0258* (2013.01); *A61M 3/0295* (2013.01); *A61M 3/0208* (2014.02);  
(Continued)

(58) Field of Classification Search  
CPC .... A61M 3/0258; A61M 3/0295; A61M 3/02; A61M 5/14; A61M 5/1411;  
(Continued)

(56) References Cited

U.S. PATENT DOCUMENTS 1,718,369 A   6/1929  Lillford  
1,901,069 A * 3/1933  Williams ............ A61M 3/0245  
                                               604/408  
(Continued)

FOREIGN PATENT DOCUMENTS

EP   2653064 A1   10/2013  
EP   2671601 B1    3/2016  
(Continued)

OTHER PUBLICATIONS

International Search Report and Written Opinion of the International Searching Authority dated Nov. 23, 2018 for International Application No. PCT/US2018/039561.

*Primary Examiner* — Phillip A Gray  
(74) *Attorney, Agent, or Firm* — Cook Alex Ltd.

(57) ABSTRACT

A collapsible liquid reservoir has a flexible side wall having a lower step, a middle step and an upper step. Each of the steps includes a riser segment and a tread segment. The riser and tread segments are pivotably connected to one another at an external hinge. When the step is collapsed its segments define an acute step angle between them of about 23°. When the step is expanded its segments define an obtuse step angle between them of about 115°. The tread of at least one step is pivotably connected to the riser of an adjacent step at an internal hinge. The step segments joined to the internal hinge (Continued)

are symmetrical about a bisector of that hinge. The reservoir has a truncated pyramid shape defined by a generally square base and four trapezoidal side panels joined to one another at corners.

18 Claims, 5 Drawing Sheets

(52) U.S. Cl.
CPC . *A61M 2205/3368* (2013.01); *A61M 2205/50* (2013.01); *B65D 21/086* (2013.01)

(58) Field of Classification Search
CPC .... B65D 21/086; B65D 1/0292; B65D 11/18; B65D 11/1806; B65D 11/1813; B65D 11/182; B65D 11/1826; B65D 11/1833; B65D 11/184; B65D 11/1846; B65D 11/1853; B65D 11/186; Y10S 220/907
See application file for complete search history.

(56) References Cited

U.S. PATENT DOCUMENTS

| | | | |
|---|---|---|---|
| 4,014,332 A * | 3/1977 | Sneider | A61M 3/0266 604/262 |
| 5,632,406 A * | 5/1997 | Robbins, III | B65D 25/325 220/666 |
| 6,354,456 B2 * | 3/2002 | Rapson | B65D 21/086 220/506 |
| 6,641,002 B2 | 11/2003 | Gerenraich et al. | |
| 7,118,050 B1 | 10/2006 | Chen | |
| 7,237,729 B2 | 7/2007 | Chen | |
| 7,347,386 B2 | 3/2008 | Chen | |
| 7,477,835 B2 | 1/2009 | Yoo | |
| 9,296,508 B2 | 3/2016 | Kanfer et al. | |
| 9,610,220 B2 | 4/2017 | Andersson et al. | |
| 2005/0127074 A1 * | 6/2005 | Kusuma | B65D 21/086 220/6 |
| 2014/0263375 A1 * | 9/2014 | Willemsen | B65D 21/086 220/666 |
| 2015/0251808 A1 * | 9/2015 | Tsui | A47L 19/04 220/8 |
| 2017/0274135 A1 * | 9/2017 | Frostaa | A61M 3/0295 |

FOREIGN PATENT DOCUMENTS

| | | | |
|---|---|---|---|
| WO | WO 03/030968 A1 | 4/2003 | |
| WO | WO-2016050977 A1 * | 4/2016 | .......... B65D 1/0292 |
| WO | WO 2018/009871 A1 | 1/2018 | |

\* cited by examiner

COLLAPSIBLE LIQUID RESERVOIR

The present application claims the benefit of and priority to U.S. Provisional Application No. 62/526,837, filed Jun. 29, 2017, which is hereby incorporated herein by reference.

FIELD OF THE DISCLOSURE

The present disclosure is directed to a collapsible and expandable liquid supply reservoir. More particularly, a portable reservoir is disclosed for medical applications such as trans-anal irrigation (TAI) or antegrade irrigation such as colostomy/stoma irrigation.

BACKGROUND

Many individuals suffering spinal cord injury and other medical conditions may need to avail themselves of bowel management treatments. Trans-anal irrigation (TAI) provides one option for bowel management. TAI is the delivery of irrigating liquid (usually water) into the colon to flush the system of stool and create pseudo-continence for the user. Systems currently on the market allow the user to utilize a product over the toilet, on a commode/shower chair or in a bed to introduce water into the bowel through a rectal catheter. The user will introduce an amount of water into the bowel (typically 500-700 mL) in order to flush out stool located in the bowel passage. The user will typically introduce the water, wait for a period of time and allow gravity to flush the water and stool out of the body. The rectal catheter may have an inflatable/deflatable balloon to assist in retention of the catheter during water introduction. A particularly suitable TAI device is shown in U.S. Patent Application Ser. Nos. 62/360,014, filed Jul. 8, 2016, and Ser. No. 62/460,502, filed Feb. 17, 2017, the disclosures of which are hereby incorporated by reference herein and which are shown in WO 2018/009871, published Jan. 11, 2018.

The typical TAI device has an irrigation liquid reservoir and a pump base unit which contains a pump for pumping water from the reservoir through suitable tubing to the catheter. Optionally the reservoir may be made separable from the pump base unit and tubing. This makes filling the reservoir easier since just the reservoir can be carried to a faucet to fill it, without the need to move the pump base unit or tubing along with the reservoir. Alternately, the reservoir may be integrated with the pump base unit.

It is desirable that when the reservoir is not in use, it can be collapsed to minimize the volume of the device for storage. When in use the reservoir expands and creates an enclosure that contains water used for irrigation and retention balloon inflation. Among the challenges faced in designing a reservoir for use with a TAI device is the reservoir must withstand long-term use wherein it will be frequently expanded and collapsed. Furthermore, users often have limited dexterity so the reservoir must perform correctly without requiring fine motor skills on the part of the user.

Problems encountered in some designs of a collapsible reservoir include: failing to collapse completely; requiring too large of a force to collapse the reservoir; failing to remain in the collapsed or expanded position as desired; substantial buckling of the reservoir walls as it is collapsed; and sagging or drooping of the walls when in the expanded position. Buckling is a torsional motion within the thicker wall segments, which leads to incomplete or unpredictable collapse and the result that the flexible wall segments do not nest together properly. The present disclosure is directed to a new reservoir design that will address these items by: causing the reservoir to expand and collapse fully and then remain in the collapsed and expanded positions as desired, i.e., there is no snapping back up or down; reducing the force required to collapse the reservoir; and eliminating any buckling or instability as the reservoir expands or collapses.

SUMMARY

In one aspect, the present disclosure concerns a water supply for a TAI or colostomy/stoma irrigation device having a reservoir mounted on a pump base unit. The reservoir is collapsible for storage and expandable for use. It has a flexible wall having a corrugated or bellows-like construction formed by three steps which are nested together. There is a lower step, a middle step and an upper step. Each step comprises a riser and a tread which are pivotably connected to one another at an external hinge. The lower and middle steps in turn are pivotably connected to one another at a first internal hinge. Similarly, the middle and upper steps are pivotably connected to one another at a second internal hinge. Finally, the upper step is pivotably connected to a collar connector at a third internal hinge.

To improve manufacturability and to minimize production costs, the reservoir of the present disclosure will be manufactured in the collapsed position. A suitable manufacturing method is compression molding, although other methods are possible. The overall shape of the reservoir can be described as a truncated pyramid. That is, the reservoir has a generally square base but with rounded corners. Its flexible wall is joined to the perimeter of the square base and comprises four trapezoidal side panels which incorporate the three steps. The trapezoidal side panels are joined to one another at rounded corners. The side panels converge toward the top where they are attached to a generally square collar at the top of the panels. The pyramidal shape of the side walls permits the reservoir to mate with a square pump base unit. Having a square pump base unit is advantageous in terms of fitting the pump, batteries, solenoid valves, tubing and circuit board in the pump base unit.

DETAILED DESCRIPTION OF THE EMBODIMENTS

Figure 1:
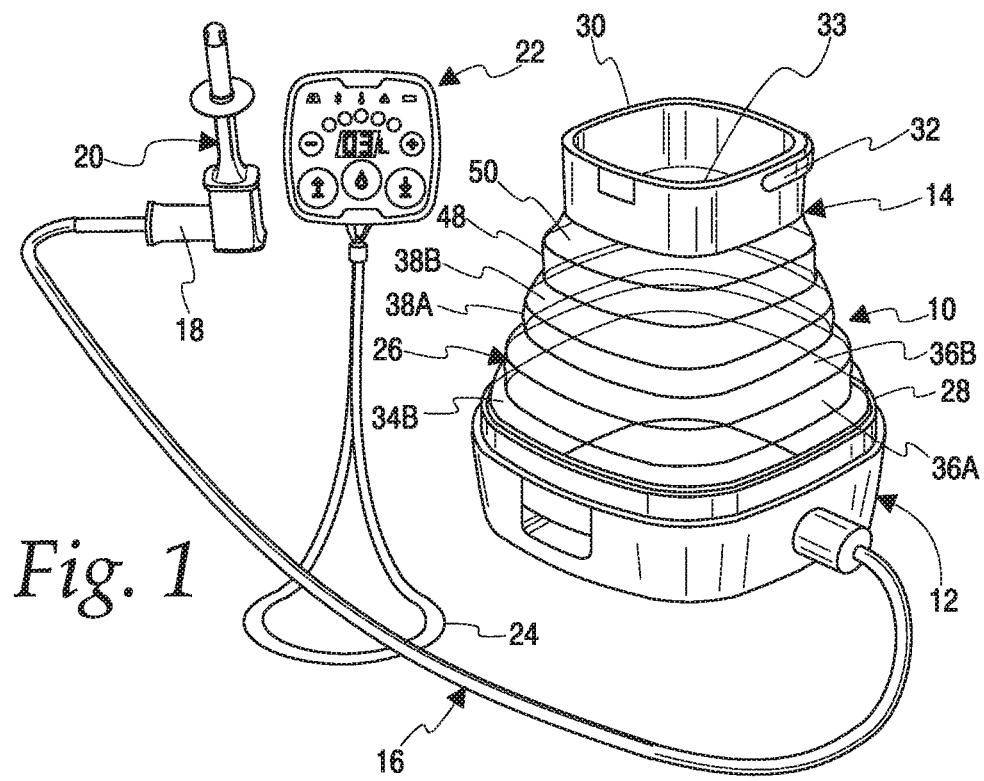
FIG. 1 is a perspective view of TAI device having the reservoir of the present disclosure, shown here mounted on the pump base unit and in the expanded position.

The present disclosure is directed to a trans-anal irrigation (TAI) device which is shown generally at 10 in FIG. 1 where it is shown deployed for use. The main components of the device 10 include a pump base unit 12, an irrigation fluid reservoir 14, fluid tubing 16, a connector hub 18, a disposable rectal catheter 20, and a wireless controller 22, with an optional lanyard 24 attached to the controller.

The reservoir 14 has a flexible side wall 26 that extends from an upstanding outer wall 28 at the bottom to a collar 30 at the top. Both the outer wall 28 and the collar 30 are relatively rigid. Although it is not shown here, it will be understood that the outer wall 28 is attached to a generally horizontal, relatively rigid bottom wall or base. The bottom wall or base has a generally square shape with rounded corners. The upstanding outer wall 28 is attached to and extends around the perimeter of the horizontal bottom wall. Preferably the bottom wall and outer wall 28 are molded as a single unit. The lower end of the flexible side wall 26 overlaps and is fixed to the interior surface of the outer wall 28 in sealing engagement. The upper end of the flexible side wall is fixed to the collar 30.

The collar 30 has a handle 32 pivotably connected to it. A user can pivot the handle up 90° from the position illustrated in FIG. 1 to carry the reservoir 14. The collar 30 defines an opening 33 at the top of the reservoir. This opening may receive a funnel (not shown) therein. The funnel may have a fill tube connected to it. The funnel can be removed from the collar 30 and placed underneath a faucet for filling the reservoir. The free end of the fill tube would be placed through the collar 30 and into the reservoir cavity for this purpose. Water from the faucet flows through the funnel and fill tube and into the reservoir 14.

It will be understood if the reservoir is removable from the pump base unit then the reservoir bottom wall will have a valve in it that provides selectable fluid communication between the interior of the reservoir and a conduit joined to one of the pump flow control valves. The valve automatically closes when the reservoir 14 is removed from the pump base unit 12 and automatically opens when the reservoir is mounted on the pump base unit 12. The pump base unit may also mount a temperature sensor (not shown) that electronically communicates with the controller 22.

The flexible side wall 26 is formed by three step sections of progressively smaller outer dimension from bottom to top. Successive riser segments of the flexible side wall are joined by an intervening tread segment. The junctions between the riser and tread segments form flexible hinges that provide an overall stair-stepped construction to the expanded reservoir. Thus, the side wall 26 functions somewhat in the nature of a bellows and permits the reservoir to be telescopically expanded (as shown in FIG. 1) during use and collapsed (as shown in FIG. 2) during storage.

Figure 2:
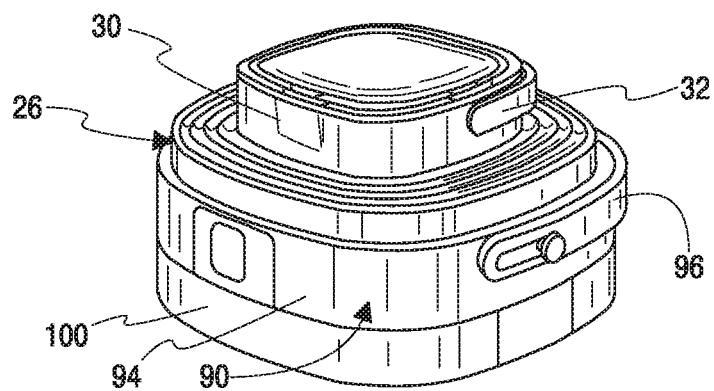
FIG. 2 is a perspective view of the pump base unit with the reservoir mounted thereon and in the collapsed position.
Figure 3:
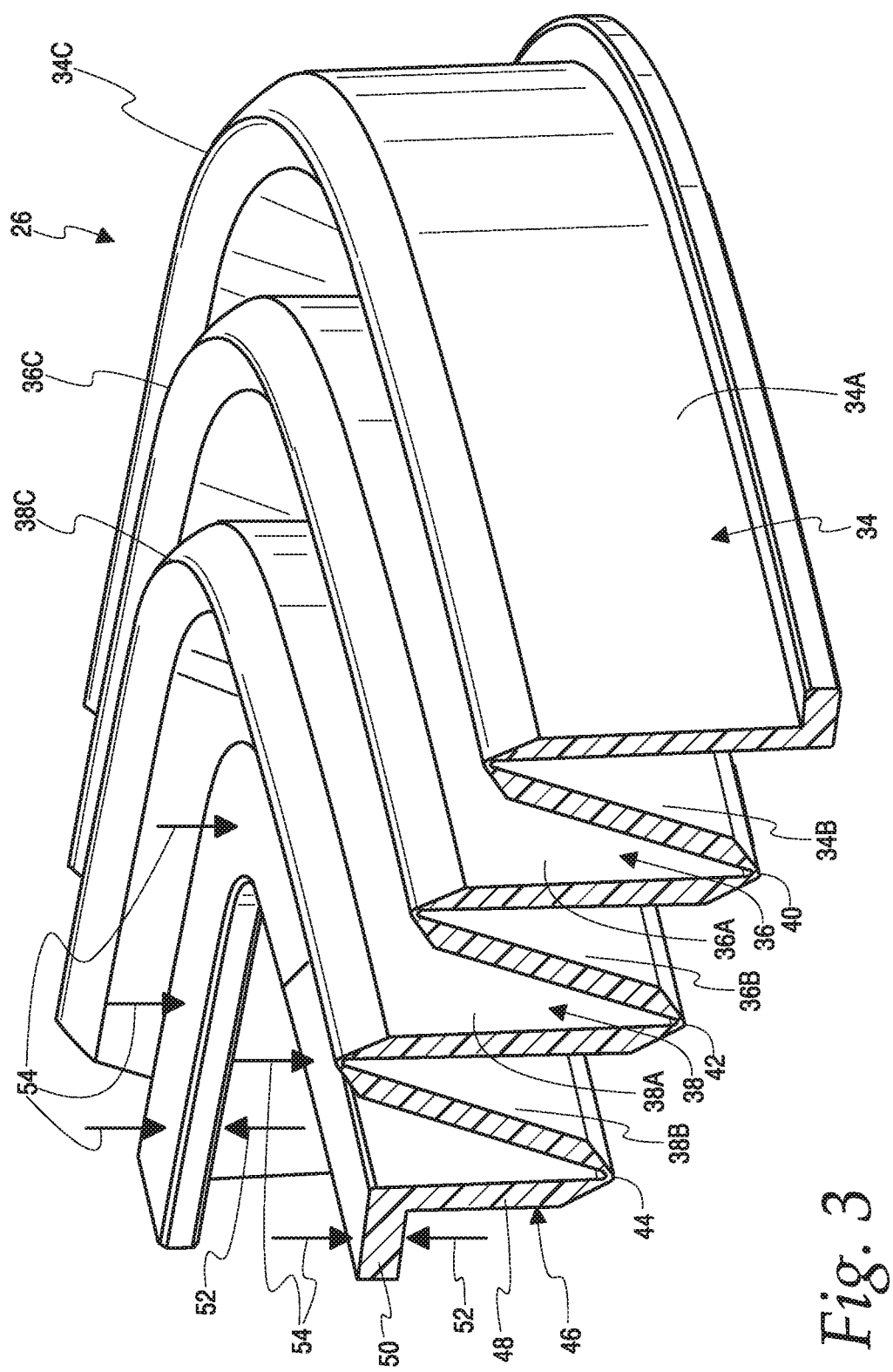
FIG. 3 is a perspective view of a quarter section of the flexible portion of the reservoir wall in the collapsed position, generally looking at the exterior of the wall.
Figure 4:
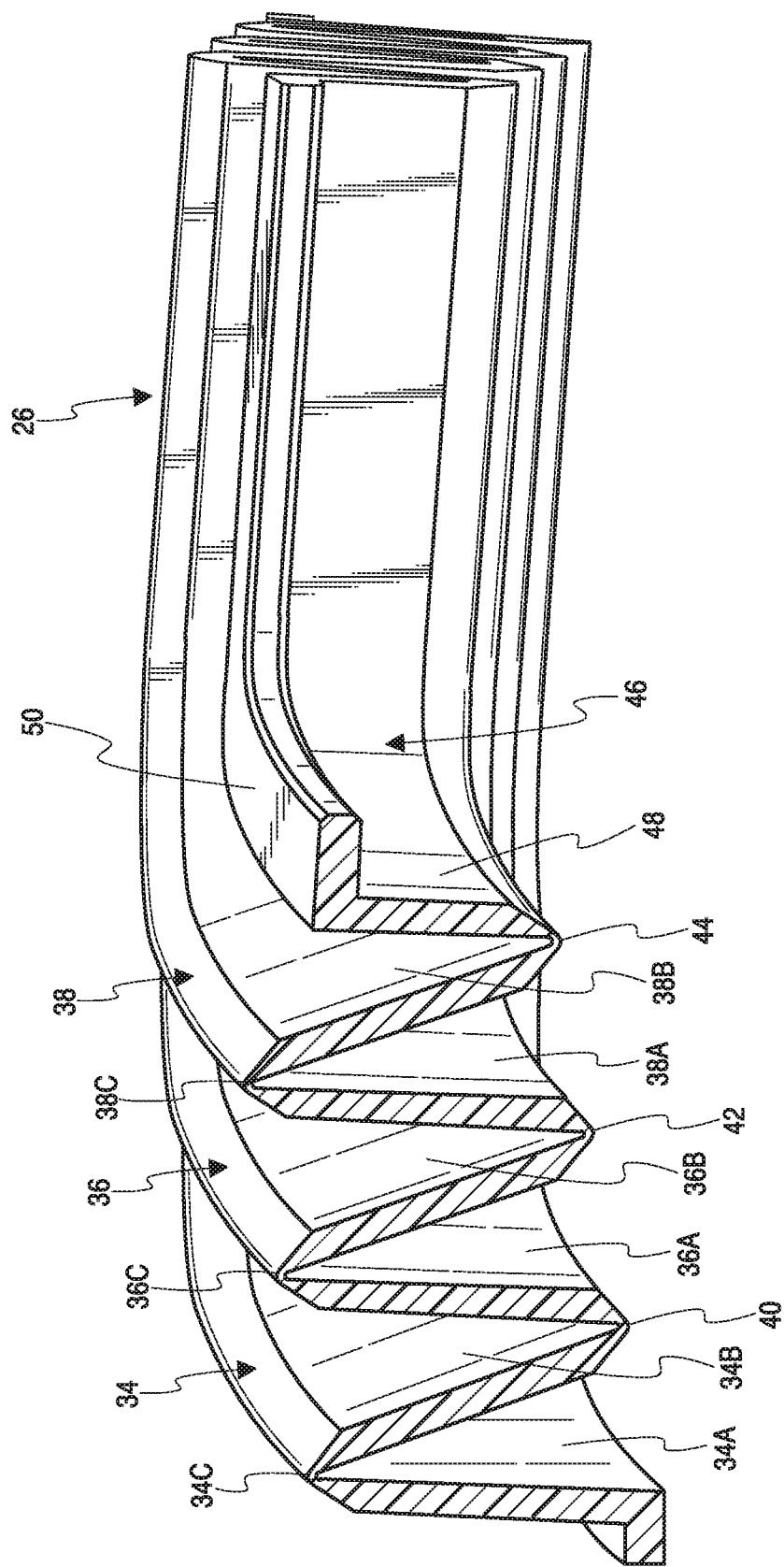
FIG. 4 is a perspective view of a quarter section of the flexible portion of the reservoir wall in the collapsed position, generally looking at the interior of the wall.

FIG. 2 illustrates a few details of the pump base unit 12. It has a generally hollow shell 90 which includes a perimeter wall 94. The wall 94 surrounds the lower portion of the outer wall 28 of the reservoir 14 when the reservoir is installed on the pump base unit 12. The wall 94 has a handle 96 pivotably connected to it. A user can pivot the handle up 90° from the position illustrated in FIG. 2 to carry the pump base unit 12. During use of the device a hollow cover 100 is removed from the top of the shell 90 and turned over to fit underneath the floor of the shell as seen in FIG. 2. During storage the cover 100 fits over the reservoir and removably joins the wall 94 to form a compact structure for storage or transport.

Further details of the flexible side wall 26 of the reservoir 14 will now be described in connection with FIGS. 3-6. The flexible side wall has a corrugated or bellows-like construction formed by three steps which are nested together. There is a lower step 34, a middle step 36 and an upper step 38.

Each step comprises a riser segment and a tread segment which are pivotably connected to one another at an external hinge. The risers for the three steps are designated 34A, 36A and 38A, respectively. The treads are designated 34B, 36B and 38B, respectively. The external hinges are designated 34C, 36C and 38C, respectively. The steps are also pivotably connected to each other. Thus, the lower and middle steps 34, 36 are pivotably connected to one another at a first internal hinge 40. Similarly, the middle and upper steps 36, 38 are pivotably connected to one another at a second internal hinge 42. Finally, the upper step 38 is pivotably connected at a third internal hinge 44 to a collar connector 46.

The collar connector 46 has a generally vertical riser segment 48 that is somewhat truncated compared to the riser segments of the steps. The riser segment 48 is integrally attached to a horizontally disposed flange 50. The flange 50 is fixed to the rigid collar 30 which forms the top of the reservoir. The upward arrows 52 in FIG. 3 indicate where an expanding force on the flange 50 would be applied. Similarly, the downward arrows 54 in FIG. 3 indicate where a collapsing force would be applied to the flange 50.

Figure 5:
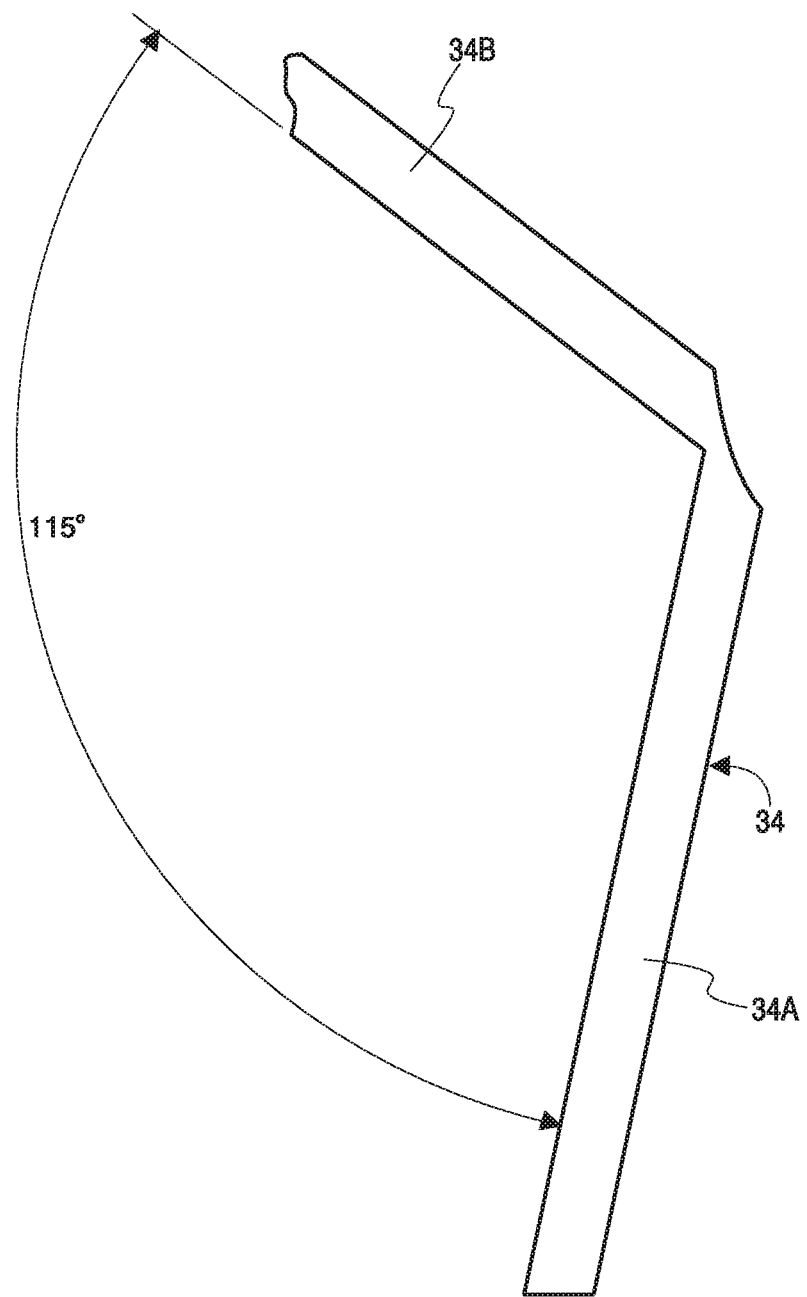
FIG. 5 is a section through the flexible portion of the reservoir wall, looking at the lower reservoir step in the expanded position.
Figure 6:
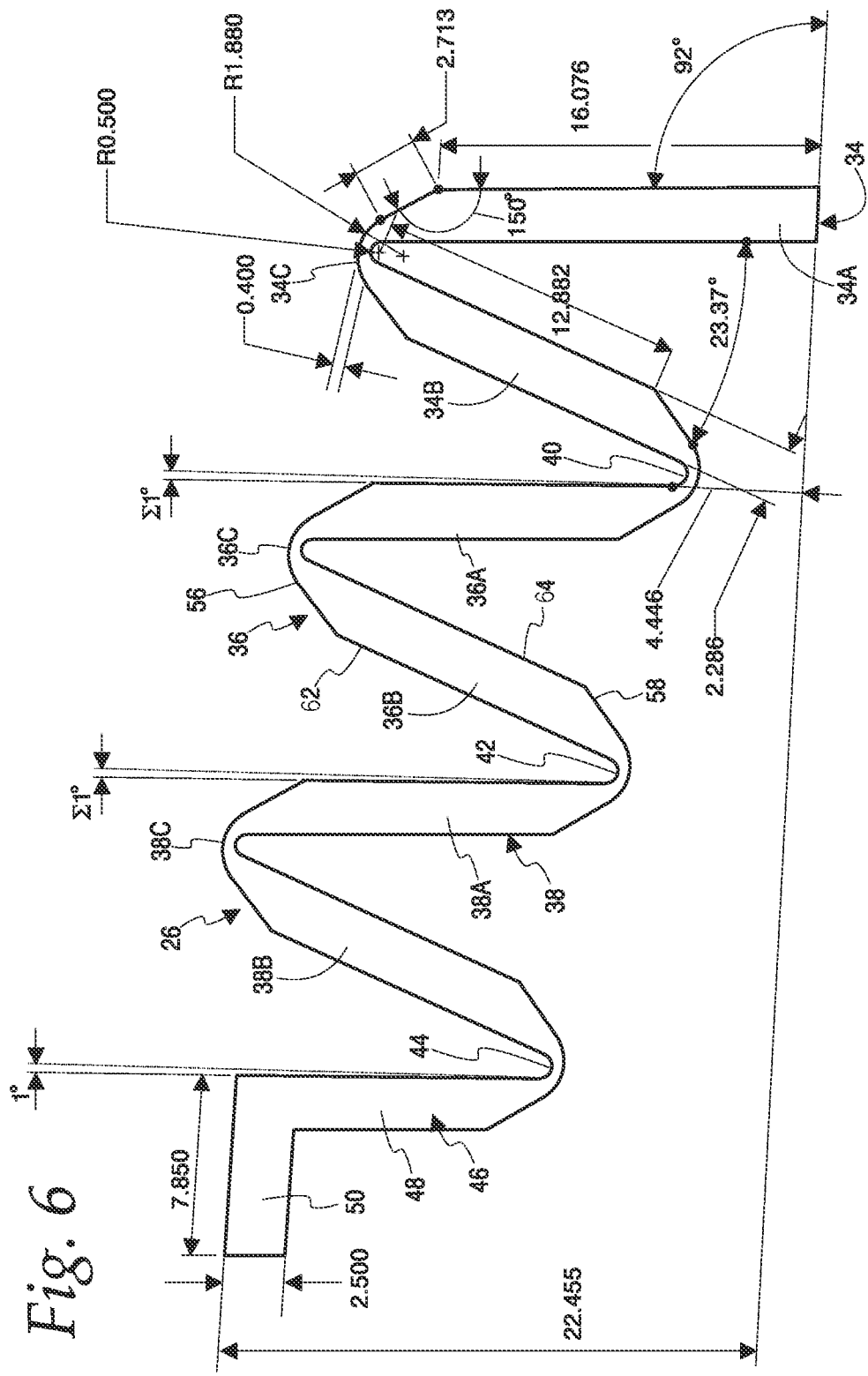
FIG. 6 is a half section through the flexible portion of the reservoir wall, looking at all of the reservoir steps in the collapsed position, with the length dimensions shown being in millimeters.

Some of the design parameters of the flexible wall are shown in FIGS. 5 and 6 and include the following:

A) The step angle is defined as the non-reflex angle between the riser and tread segments of a particular step. There is an obtuse step angle, when the reservoir is expanded, and an acute step angle, when the reservoir is collapsed. As seen in FIG. 6 the collapsed, acute step angle is 23.37°. As seen in FIG. 5 the expanded, obtuse step angle is 115°. Both step angles are measured after a user expands or collapses the reservoir and releases it to a stable position.

B) The segment thickness is shown for tread 34B as 2.286 mm.

C) The riser length is shown for riser 34A as 16.076 mm.

D) The tread length is shown for tread 34B as 12.882 mm.

E) A first, straight angled run portion of the external hinge 34C, i.e, the hinge length, is shown as 2.713 mm.

F) The inside radius of external hinge 34C is shown as R0.500 mm.

G) The outside radius of external hinge 34C is shown as R1.880 mm.

H) The hinge thickness of external hinge 34C is shown as 0.400 mm.

I) The hinge angle between the outer surface of the riser 34A and the first angled run portion of the external hinge 34C is shown as 150°.

It has been found that the dimensions and geometry of the step segments and hinges are important to making the reservoir perform as desired. In particular, the collapsed, acute step angle must be greater than 18° and more preferably greater than 23°. The hinge thickness must be less than 0.8 mm and more preferably about 0.4 mm. The expanded, obtuse step angle must be greater than 110° but no more than 115° and more preferably 115°. Similarly, the number of steps in combination with the foregoing preferences was found to be important as well. Limiting the number of steps to three and limiting the obtuse step angle when expanded to about 115° allows all hinges to fold properly.

The reservoir is manufactured using silicone rubber (durometer 50 Shore A). The material durometer does not impact the dynamics of the reservoir as it is expanded and collapsed, but it will change the force required by the user to collapse or expand it. The material could have different characteristics and can be easily changed once a tool has been built. The material properties may be as shown in the following table:

TABLE 1

| Material Properties | |
|---|---|
| Parameter | Value |
| Young's Modulus | 1.707 MPa |
| Poisson's Ratio | 0.3 |
| Tensile Strength | 6.6 MPa |
| Yield Strength | 12.2 MPa |
| Density | 2e–6 kg/m³ |

In this table the durometer (50 Shore A) is converted to Young's Modulus using the formula: exp((Shore-A Durometer)*0.0235–0.6403). The tensile strength and yield strength value were obtained from Silicone Material Selection Guide.

With the design as shown all collapsing and expansion motion is isolated to the thin hinge sections while the thicker segments remain essentially rigid. It is preferred that the flexible portion of the reservoir be molded in the collapsed position as it is easier to manufacture this way. A draft angle of greater than 0.5° is preferred, such as the 1.0° draft angle shown in FIG. 6.

Further, it will be noted that other than riser 34A, the flexible wall 26 of FIG. 6 shows the adjacent pairs of step segments are mirror images of each other. For example, tread 34B is a mirror image of its immediate neighbor, riser 36A and riser 36A is a mirror image of tread 36B, and so on. Riser 34A is not a mirror image of its tread 34B because riser 34A is longer than tread 34 and does not have a hinge formed at its base. Thus, the step segments are symmetric about bisectors through internal hinges 40 and 42 and external hinges 36C and 38C.

It is also pointed out that the cross-sections of symmetric step segments 34B, 36A, 36B, 38A and 38B are parallelograms. As seen in FIG. 6, each segment has an elongated external face (one of which is designated 62) and an elongated internal face (one of which is designated 64). Elongated faces 62 and 64 are parallel to one another. Then at each end there is an angled run extending from the elongated face to the arcuate portions of the hinge. Thus, the external face 62 joins an angled run 56 and the internal face 64 joins an angled run 58. The angled runs 56, 58 are parallel to one another. This segment shape assures that the folding of the steps occurs at the hinges and that the elongated body portions of the step will not buckle.

It should be understood that various changes and modifications to the presently preferred embodiments described herein will be apparent to those skilled in the art. Such changes and modification can be made without departing from the spirit and scope of the invention disclosed herein.

What is claimed is:

1. An irrigation device comprising:
a collapsible reservoir, comprising:
   a top including an opening;
   a bottom wall; and
   a flexible side wall having a lower step, a middle step and an upper step, wherein the steps are of progressively smaller outer dimension from bottom to top, each of the steps comprising a riser segment and a tread segment pivotably connected to one another at an external hinge, each step when collapsed defining an acute step angle between the riser and tread segments of about 23° such that the upper and middle steps nest inward within the lower step and each step when expanded defining an obtuse step angle between the riser and tread segments of from about 110° to about 115°, the tread of the lower step being pivotably connected to the riser of the middle step at a first internal hinge, and the tread of the middle step being pivotably connected to the riser of the upper step at a second internal hinge;
an irrigation catheter; and
a tubing one end of which is operably connected to the reservoir and the other end connected to the irrigation catheter.

2. The irrigation device of claim 1 wherein each of the hinges have a hinge thickness of about 0.4 mm.

3. The irrigation device of claim 2 wherein the internal and external hinges each have an internal radius of about 0.500 mm and an external radius of about 1.880 mm.

4. The irrigation device of claim 3 wherein the riser and tread segments have a width of about 2.286 mm.

5. The irrigation device of claim 4 wherein the internal and external hinges comprise a first angled run portion whose length is about 2.713 mm.

6. The irrigation device of claim 5 wherein the hinge angle between the first angled run portion and its adjacent riser segment is about 150°.

7. The irrigation device of claim 6 wherein the riser segment of the lower step has a length of about 16.076 mm.

8. The irrigation device of claim 7 wherein the tread segment of the lower step has a length of about 12.882 mm.

9. The irrigation device of claim 1 further comprising a collar connector pivotably connected to the tread of the upper step at a third internal hinge.

10. The irrigation device reservoir of claim 9 wherein the collar connector has a vertical riser segment connected to a horizontally disposed flange.

11. An irrigation device comprising:
a collapsible reservoir, comprising:
   a top including an opening;
   a bottom wall; and
   a flexible side wall having a plurality of steps, wherein the steps are of progressively smaller outer dimension from a bottom step to a top step, each of the steps comprising a riser segment and a tread segment pivotably connected to one another at an external hinge, the tread of at least one step being pivotably connected to the riser of an adjacent step at an internal hinge, and the step segments joined to the internal hinge being symmetrical about a bisector of said internal hinge such that the steps nest inward from the bottom step when collapsed;
an irrigation catheter; and
a tubing one end of which is operably connected to the reservoir and the other end connected to the irrigation catheter.

12. The irrigation device of claim 11 wherein one of said steps is a lower step having a lower riser and at least some of the step segments other than the lower riser have a cross section in the shape of a parallelogram with parallel elongated faces and angled runs at the ends.

13. An irrigation device comprising:
a collapsible reservoir, comprising:
   a top including an opening;
   a bottom wall; and
   a flexible side wall having a plurality of steps, each of the steps comprising a riser segment and a tread segment pivotably connected to one another at an external hinge, the tread of at least one step being pivotably connected to the riser of an adjacent step at an internal hinge, wherein the steps are of progressively smaller outer dimension from a bottom step to a top step such that the steps nest inward from the bottom step when collapsed, the flexible side wall having the shape of a truncated pyramid having a generally square base and four trapezoidal side panels joined to one another at corners;

an irrigation catheter; and a tubing one end of which is operably connected to the reservoir and the other end connected to the irrigation catheter.

14. The irrigation device of claim 13 wherein the step segments joined to the internal hinge are symmetrical about a bisector of said internal hinge.

15. The irrigation device of claim 13 wherein one of said steps is a lower step having a lower riser and at least some of the step segments other than the lower riser have a cross section in the shape of a parallelogram with parallel elongated faces and angled runs at the ends.

16. The irrigation device of claim 9, wherein the collar defines the opening at the top of the reservoir.

17. The irrigation device of claim 16, wherein the opening is configured to receive a funnel.

18. The irrigation device of claim 1, wherein the obtuse step angle is about 115°.

* * * * *